United States Patent [19]

Ecsery et al.

[11] Patent Number: 5,008,292
[45] Date of Patent: Apr. 16, 1991

[54] PESTICIDAL METHOD

[75] Inventors: Zoltán Ecsery; József Knoll; Eva Somfai; Zoltán Török; Éva Szinnyei; Károly Mozsolits, all of Budapest, Hungary

[73] Assignee: Chinoin Gyogyszer Es Vegyeszeti Termekek Gyara R. T., Budapest, Hungary

[21] Appl. No.: 129,342

[22] Filed: Nov. 25, 1987

Related U.S. Application Data

[63] Continuation of Ser. No. 739,185, May 30, 1985, abandoned.

[30] Foreign Application Priority Data

May 31, 1984 [HU] Hungary ................. 2124/84

[51] Int. Cl.⁵ ............... A01N 33/04; C07C 211/03
[52] U.S. Cl. ........................ 514/654; 564/381
[58] Field of Search ............... 564/381, 382; 514/654

[56] References Cited

U.S. PATENT DOCUMENTS

| | | | |
|---|---|---|---|
| 3,142,554 | 7/1964 | Godfrey | 564/341 X |
| 3,221,054 | 11/1965 | Arnold et al. | 564/353 |
| 3,429,922 | 2/1969 | Berezi et al. | 564/381 |
| 3,485,874 | 12/1967 | Ecsery et al. | 564/381 |
| 3,496,195 | 2/1970 | Ecsery et al. | 564/381 |
| 3,689,504 | 9/1972 | Horrom | 564/382 X |
| 4,137,328 | 1/1979 | Cox et al. | 564/341 X |
| 4,156,017 | 5/1979 | Kruger et al. | 564/384 X |
| 4,200,654 | 4/1980 | Stein et al. | 564/341 |

OTHER PUBLICATIONS

Burger, Medicinal Chemistry, Third Edition, vol. 1, pp. 74–76 (1970).
Experientia vol. 31, No. 9, pp. 1015–1017 (1975).
Keyserling et al., Approaches to New Leads for Insecticides, pp. 117–129, Berlin 1985.
Pyrethrum Post, No. 2, vol. 6, Oct. 1961, p. 12.
J. Econ. Entomol. 78, pp. 722–724 (1985).
R. M. Hollingworth, A. E. Lund: Effects of Amidine Pesticides, pp. 209–210.

*Primary Examiner*—Richard L. Raymond
*Attorney, Agent, or Firm*—Herbert Dubno

[57] ABSTRACT

The invention relates to N-[2-(4-fluorophenyl)-1-methyl]-ethyl-N-methyl-N-propynyl amine of the Formula I

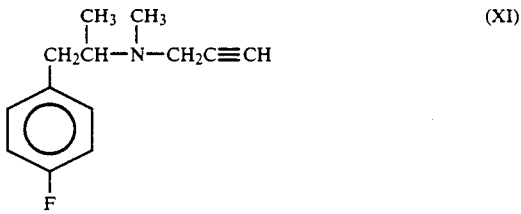

and isomers and salts thereof.

The compound of the Formula I is useful as an insecticide.

3 Claims, No Drawings

PESTICIDAL METHOD

This is a continuation of co-pending application Ser. No. 739,185 filed on May 30, 1985, now abandoned.

This invention relates to a new phenyl-isopropyl amine derivative, a process for the preparation thereof, pesticidal compositions comprising the same and a method for combating pests.

In U.S. Pat. Nos. 3,485,874 and 3,496,195 a process is described for the preparation of phenyl isopropyl amine derivatives substituted by bromine in the ortho- and para-positions and optionally active derivatives thereof. According to the said U.S. Patent Nos. the o- and p-bromo-phenyl isopropyl methyl amines described in U.S. Pat. No. 3,485,874 possess coronary dilatory, hallucinogenic, depressant, tranquillant, analgesic and catabolic anorexic properties while the optically active D-o-bromo-phenyl-isopropyl-methyl-propynyl amine disclosed in U.S. Pat. No. 3,496,195 exhibits monoaminooxidase (MAO) inhibitory effect.

It is known furtheron (U.S. Pat. No. 4,156,017) that certain MAO-inhibitors possess insecticidal properties as well. It is, however, also disclosed in the said U.S. Patent No. that not all MAO-inhibitors exhibit insecticidal effect and at the same time a method is protected by which insecticidal effect is produced on certain insects by using N-benzyl-N-methyl-propynyl amine or a chlorinated or methoxylated derivative thereof in position(s) 2, 3 and/or 4. Since the reported insecticidal effect is relatively low, the reference compounds are relatively toxic to mammals and the compounds are relatively expensive, not a single representative of the group has been used so far as a pesticide.

It is the object of the present invention to provide new phenyl-isopropyl amine derivatives suitable for use in agriculture as pesticides.

According to the present invention there is provided the new N-[2-(4-fluoro-phenyl)-1-methyl]ethyl-N-methyl-N-propynyl amine of the Formula I and isomers and salts thereof.

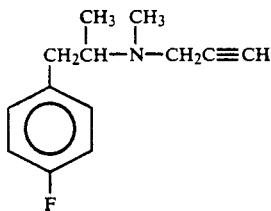

(XI)

The compound of the Formula I and isomers and salts thereof are new and have not been disclosed in the prior art.

The compound of the Formula I and isomers and salts thereof possess excellent pesticidal—particularly insecticidal—properties.

The compound of the Formula I contains an asymmetrical carbon atom and may be present as a racemate or an optically active antipode. The compound of the Formula I is of a basic character and forms salts with acids. In the present specification the term "compound of the Formula I" encompasses the racemate, the optically active antipodes and the salts as well. The scope of protection is extended to all possible isomers and salts.

The present invention is based on the recognition that in the group of N-alkyl-N-phenyl-alkyl-amines—the compound of the present invention belongs to the said compound-group—the position and character of the substituents of the phenyl ring effects the molecule to such a large extent that any generalization may lead to errors.

Thus the specific biological activity found within the framework of the present invention was not aforeseen on the basis of the compounds known from and specifically disclosed in the prior art.

According to a feature of the present invention there is provided the new compound of the Formula I and optically active antipodes and salts thereof.

The Formula I encompasses the following compounds:

(±)-N-[2-(4-fluoro-phenyl)-1-methyl]-ethyl-N-methyl-N-propynyl amine and its salts;

(−)-N-[2-(4-fluoro-phenyl)-1-methyl]-ethyl-N-methyl-N-propynyl amine and its salts;

(+)-N-[2-(4-fluoro-phenyl)-1-methyl]-ethyl-N-methyl-N-propynyl amine and its salts.

According to a further feature of the present invention there is provided a process for the preparation of N-[2-(4-fluoro-phenyl)-1-methyl]-ethyl-N-methyl-N-propynyl-amine and isomers and salts thereof, which comprises reacting a 2-phenyl-isopropyl derivative of the Formula II with a compound of the Formula III $$B—R^1 \qquad (III)$$

wherein $R^1$ stands for methyl or propynyl or a group which may be converted into methyl or propynyl;

$R^2$ is fluorine or a group which may be converted into fluorine;

A and B represent groups which on reacting with each other are capable of forming a bivalent group of the Formula

or comprise the said bivalent group and A may be attached to the carbon atom by a single or double bond—whereby in the latter case it can not bear a hydrogen if necessary converting in the amine of the Formula V obtained the $R^2$ group into fluorine; and/or if necessary forming in the amine of the Formula IV obtained the propynyl group in one or more steps; and/or subjecting a compound of the Formula XIII (wherein $R^2$ has the same meaning as stated above) to N-methylation; whereby the three latter steps may be carried out in an optional order; and if desired converting a propynyl amine of the Formula I obtained into a salt formed with a mineral or organic acid or setting free the base from a salt thereof.

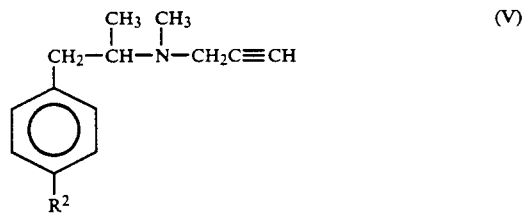

(V)

-continued

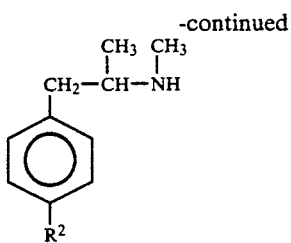
(IV)

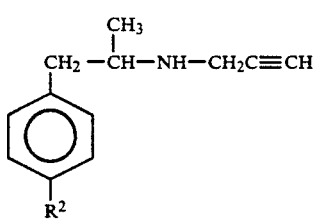
(XIII)

According to a form of realization of the process of the present invention an amine of the Formula VIII

(VIII)

wherein $R^4$ stands for hydrogen or an optionally halo-substituted, saturated or unsaturated aliphatic hydrocarbon group having 3 carbon atoms and $R^5$ is hydrogen or methyl with a phenyl acetone derivative of the Formula IX

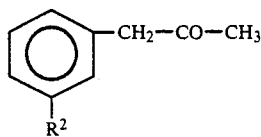
(IX)

(wherein $R^2$ is as stated above). In this reaction the corresponding ketimine or oxyamine is formed as intermediate which is thereafter reduced. Reduction may be carried out by methods known per se. Catalytic hydrogenation or nascent hydrogen may be used. In the compound thus obtained the $R^4$ group is converted into propynyl and/or the $R^5$ group into methyl, if necessary. The said reactions may be carried out in optional order.

According to an other form of realization of the process of the present invention an amine of the Formula VIII is reacted with a phenyl isopropyl derivative of the Formula X

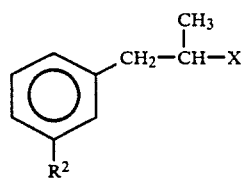
(X)

wherein $R^2$ is as stated above and X stands for halogen or a sulfonic acid group. X as halogen may be preferably chlorine, bromine or iodide. X as sulfonic acid ester group may be preferably an alkyl sulfonyloxy e.g. methyl sulfonyloxy or aryl sulfonyloxy preferably benzene sulfonyloxy, p-toluene-sulfonyloxy or p-bromo-sulfonyloxy, etc. The reaction may be carried out advantageously in the presence of an acid binding agent. In the compound thus obtained $R^2$ may be converted into fluorine and/or $R^4$ into propynyl and/or $R^5$ into methyl, if necessary. The said reactions may be carried out in optional order.

According to a still further form of realization of the process of the present invention an amine of the Formula XI

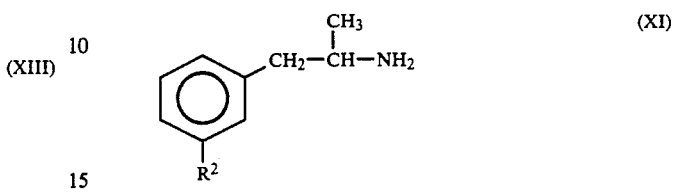
(XI)

wherein $R^2$ is as stated above is subjected to methylation and propynylation. The said reactions may be carried out in optional order.

Propynylation may be accomplished stepwise by introducing first a halopropyl or propenyl group into the molecule.

Thus one may proceed by reacting the amine of the Formula XI with 1,2-dibromo-propene and converting the 2-bromo-propenyl derivative thus obtained into the desired propynyl derivative by splitting off hydrogen bromide. This reaction may be carried out by reacting the 2-bromo-propenyl derivative with a base or subjecting the same to thermal treatment.

The methylation reaction according to the present invention may be carried out by reacting an amine of the Formula XIII

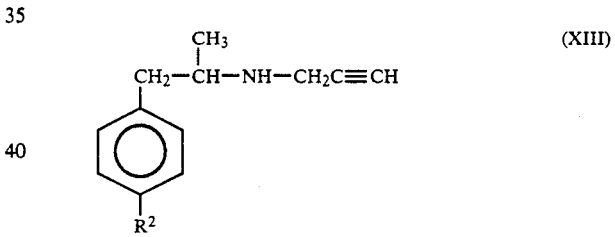
(XIII)

wherein $R^2$ is as stated above with formaldehyde and formic acid. One may also proceed by reacting an amine of the Formula XIII with a methyl ester. As methylating agent a methyl halide e.g. methyl bromide, dimethyl sulfate, methyl sulfuric acid or trimethyl phosphate may be used.

According to the another form of realization of the process of the present invention into compounds, which do not contain fluorine, a fluorine atom is introduced at any suitable stage of the synthesis. One may also proceed by using a compound of the Formula VI

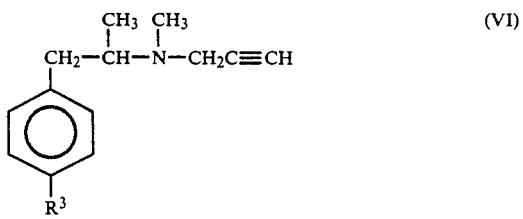
(VI)

or

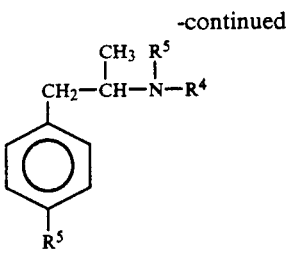

as starting material wherein $R^3$ stands for nitro, amino or diazonium and $R^4$ and $R^5$ are as stated above. The reaction may be carried out by reducing the nitro-group into an amino group, diazotizing the amino group, converting the diazonium group into diazonium-fluoroborate and forming the fluorine substituent via the latter group.

The process of the present invention encompasses the preparation of the compound of the Formula I in racemic and optically active form. If optically uniform antipodes are to be prepared a resolution step is to be accomplished at any suitable stage of the synthesis. Resolution may be carried out at the initial stage of the synthesis on a starting material. In this case a laevo- or dextrorotatory starting material of the Formula II, IV, V, VII or VIII

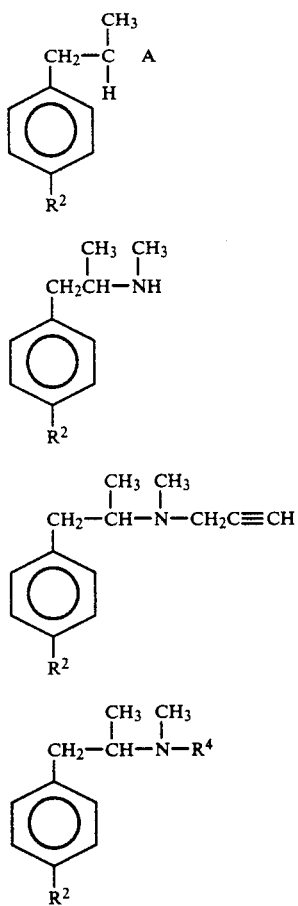

is used in the synthesis [C.A. 14 (1920) 745; Hungarian patent specifications Nos. 154,635 and 169,844].

One may also proceed by subjecting a compound of the Formula I or VI to resolution. The reaction may be carried out by methods known per se by forming a diastereomer pair of salts by using a suitable optically active acid e.g. tartaric acid or dibenzoyl tartaric acid.

The compound of the Formula I in free base form is an oily lipide-soluble substance. The compound of the Formula I may be converted into a crystalline water-soluble salt or may be set free from a salt thereof. Salt formation may be carried out by methods known per se by reacting the compound of the Formula I with a mineral or organic acid, e.g. hydrochloric acid, hydrogen bromide, sulfuric acid, phosphoric acid, acetic acid, formic acid, maleic acid, tartaric acid, lactic acid, 3,5-dinitro-benzoic acid, citric acid or oxalic acid.

According to a still further feature of the present invention there are provided pesticidal—particularly insecticidal—compositions comprising as active ingredient the compound of the Formula I or an isomer or salt thereof in admixture with suitable solid carriers and/or liquid diluents and if desired with auxiliary agents.

The pesticidal compositions may be prepared by admixing a compound of the Formula I or an isomer or acid thereof with suitable inert carriers and/or diluents and/or auxiliary agents.

According to a still further feature of the present invention there is provided a method for combating pests—particularly insects—which comprises applying onto the plants to be protected or onto the pests or the environment thereof an effective amount of a pesticidal composition according to the present invention.

The products according to our invention can be formulated into ready to use pesticidal compositions e.g. by using the following methods known per se:

Dusts are admixtures of the active ingredients with finely divided solids such as talc, attapulgite clay, kieselgur, pyrophyllite, chalk, diatomaceous earths, calcium phosphates, calcium and magnesium carbonates, sulfur, flours, and other organic and inorganic solids which act as dispersants and carriers for the toxicant. These finely divided solids have an average particle size of less than about 50 microns. A typical dust formulation useful herein contains 10.0 parts of any of our products, 30.0 parts of bentonite clay, and 60.0 parts of talc.

The compounds of the present invention may be made into liquid concentrates by solution or emulsion in suitable liquids, and into solid concentrates by admixtures with talc, clays and other known solid carriers used in the insecticide art. The concentrates are compositions containing about 5–50% toxicant, and 95–50% inert material which includes dispersing agents, and wetting agents. The concentrates are diluted for practical application, with water or other liquid for sprays or with additional solid carrier for use as dusts. Typical carriers for solid concentrates also called wettable powders include fuller's earth, kaolin clays, silicas, and other highly absorbent, readily wet inorganic diluents. A solid concentrate formulation useful herein contains 1.5 parts each of sodium lignosulfonate and sodium laurylsulfate as wetting agents, 25.0 parts of any of our products and 72.0 parts of bentonite clay.

Useful liquid concentrates include the emulsifiable concentrates, which are homogeneous liquid or paste compositions readily dispersed in water or other dispersant, and may consist entirely of the toxicant with a liquid or solid emulsifying agent, or may also contain a liquid carrier such as xylene, heavy aromatic naphthas, isophorone and other non-volatile organic solvents. For application, these concentrates are dispersed in water or other liquid carrier, and normally applied as a spray to the area to be treated.

Typical wetting, dispersing or emulsifying agents used in insecticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polethylene oxides; sulfonated animal and vegetable oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1-15% by weight of the insecticidal composition.

Other useful formulations include simple solutions of the active ingredient in a solvent in which it is completely soluble at the desired concentration, such as acetone or other organic solvents.

The concentration of the toxicant is the dilution generally used for application is normally in the range of about 2% to about 0.001%. Many variations of spraying and dusting compositions in the art may be used, by substituting a compound of this invention into compositions known or apparent to the art.

Insecticidal compositions may be formulated and applied with other active ingredients, including other insecticides, nematicides, acaricides, fungicides, plant regulators, fertilizers, etc. In applying the chemicals, it is obvious that an effective amount and concentration of our product has to be used.

The compound of the present invention exerts the insecticidal effect particularly on eggs and juvenile forms of Lepidopterae, Dipterae and Coleopterae. Since the contact effect of the compound of the Formula I is slighter, the activity is exerted particularly on long-lasting oral application. The advantage of the compound of the invention is that in addition to eliminating the insect pests it provides a high selectivity by protecting various useful insects. This property enables the introduction of the compound of the present invention into integrated pest management programs. Symptoms observed in activity tests—particularly on larvae—indicate that the action of mechanism of the compound of the present invention differs from that of conventional insecticides e.g. chlorinated hydrocarbons, phosphate esters, etc. It is presumable that the pesticidal compositions of the present invention are highly suitable for the elimination and control of pest populations resistant against conventional pesticides. Thus the compositions of the present invention are useful in delaying the development of resistance by using combinations with conventional insecticides in a proper program of rotation.

Further details of the present invention are to be found in the following Examples without limiting the scope of protection to the said Examples. The preparation of the starting materials—particularly that of the fluoro-substituted compounds—was not described in prior art and is disclosed in the Examples.

EXAMPLE 1

8.28 g. (0.0495 mole) of ($\pm$)-N-methyl-[2-(4-fluoro-phenyl)-1-methyl]-ethyl amine (J. Am. Chem. Soc. 68 1009-1011) are dissolved in 45 ml. of toluene. To the solution 0.078 g. of benzyl triethyl ammonium chloride are added and parallelly 6.48 g. (0.0545 mole) of propargyl bromide and a solution of 2.17 g. (0.0543 mole) of sodium hydroxide in 7.5 ml. of water are added dropwise under stirring within 5 minutes. The temperature of the reaction mixture rises from 23° C. to 26° C. The reaction mixture is stirred at 26°-28° C. for 20 hours whereupon the two phases are separated, the toluene layer is dried over anhydrous sodium sulfate and evaporated. The residue is distilled off at 80°-82° C./0.1 Hgmm. Thus 5.05 g. of ($\pm$)-N-methyl-N-propynyl-[2-(4-fluoro-phenyl)-1-methyl]-ethyl amine are obtained, $n_D^{20} = 1.5050$. The hydrochloride melts at 132°-133° C. (from ethanol and ether).

Analysis: for the Formula $C_{13}H_{17}NCIF$. Calc.: C %=65.59, H %=7.09, N %=5.79, Cl %=14.66, F %=7.85; Found: C %=65.00, H %=6.97, N %=5.95, Cl %=14.90, F %=8.01.

EXAMPLE 2

3.38 g. (0.022 mole) of ($\pm$)-N-methyl-[2-(4-fluoro-phenyl)-1-methyl]-ethyl amine are dissolved in 35 ml. of acetone, whereupon 19 g. (0.14 mole) of potassium carbonate are added and 2.95 g. (0.025 mole) of distilled propargyl bromide are added dropwise under stirring within 10 minutes. The temperature of the mixture rises from 22° C. to 25° C. The reaction mixture is heated at 55° C. for three hours and a half under stirring. The reaction mixture is allowed to stand overnight, filtered, washed three times with 25 ml. of acetone each and the acetone filtrate is evaporated. The residue is distilled off at 2 Hgmm. Thus 2.28 g. of ($\pm$)-N-methyl-N-propynyl-[2-(4-fluoro-phenyl)-1-methyl]-ethyl amine are obtained, yield 51.7%. Bp.: 120°-122° C./2 Hgmm., $n_D^{20} = 1.5050$.

EXAMPLE 3

30.97 g. (0.197 mole) of ($\pm$)-N-methyl-[2-(4-fluoro-phenyl)-1-methyl]-ethyl amine are dissolved in 310 ml. of acetone whereupon 174.5 g. (1.26 mole) of potassium carbonate are added and a 68% toluene solution of propargyl bromide (39.7 g., 0.227 mole) is added dropwise under stirring within 20 minutes. The temperature of the mixture rises from 26° C. to 40° C. The reaction mixture is stirred at 55° C. for six hours and a half, filtered, washed with acetone and the acetone filtrate is evaporated. The residue is distilled off at 0.6 Hgmm. Thus 16.25 g. of ($\pm$)-N-methyl-N-propinyl-[2-(4-fluoro-phenyl)-1-methyl]-ethyl amine are obtained, yield: 41.2%. Bp.: 90°-92° C.

EXAMPLE 4

7.4 g. (0.0443 mole) of ($-$)-N-methyl-[2-(4-fluoro-phenyl)-1-methyl]-ethyl amine ($[\alpha]_D^{20} = -3.44°$ ethanol)) are dissolved in 60 ml. of acetone whereupon 28.9 g. (0.21 mole) of potassium carbonate are added and a 60% toluene solution of 7.56 g. (0.045 mole) of propargyl bromide is added dropwise under stirring. The reaction mixture is stirred at 35°-40° C. for 3-4 hours, filtered, washed with acetone and the acetone filtrate is evaporated. The residue is distilled off at 2 Hgmm. Thus 3.3 g. of ($-$)-N-methyl-N-propynyl-[2-(4-fluoro-phenyl)-1-methyl]-ethyl amine are obtained, b.p.: 120°-122° C., $n_D^{20} = 1.5052$. The hydrochloride melts at 169°-171° C. $[\alpha]_D^{20} = -6.2°$ (ethanol, c=2.4); $[\alpha]_D^{20} = -10.98°$ (water, c=2.9)

EXAMPLE 5

An aqueous solution of 10 g. (0.028 mole) of ($-$)-N-methyl-[2-(4-fluoro-phenyl)-1-methyl]-ethyl amine (+)-tartarate-dihydrate (mp.: 88°-91° C.) is made alkaline with a 40% aqueous sodium hydroxide solution (pH 12-13). The solution is extracted with dichloro methane and the dichloro methane extract is dried over sodium sulfate.

To the above dichloro methane solution 22.5 g. (0.16 mole) of potassium carbonate are added whereupon 60% toluene solution of 5.96 g. of propargyl bromide is added dropwise. The reaction mixture is stirred at room temperature for 5 hours, filtered and the filtrate is extracted first four times with 25 ml. of 20% acetic acid each and thereafter four times with 25 ml. of 10% hydrochloric acid each. The aqueous hydrochloric acid extracts are made alkaline with a 40% sodium hydroxide solution and extracted with dichloro methane. The dichloro methane solution is dried and gaseous hydrogen chloride is introduced. On addition of petrolether 2.38 g. of (−)-N-methyl-N-propynyl-[2-(4-fluoro-phenyl)-1-methyl]-ethyl amine hydrochloride are obtained. Mp.: 168°-170° C. $[\alpha]_D^{20} = -10.89°$ (water, c=2.5). Yield: 47.1%.

EXAMPLE 6

From 10 g. (0.028 mole) of (−)-N-methyl-[2-(4-fluoro-phenyl)-1-methyl]-ethyl amine-(+)-tartrate dihydrate the base is set free as described in Example 5 whereupon the dichloro methane solution is evaporated. The residue is dissolved in 60 ml. of acetone, 22.5 g. (0.16 mole) of potassium carbonate are added and a 60% toluene solution of 5.96 g. of propargyl bromide is added dropwise. The reaction mixture is stirred at room temperature for 3 hours, filtered and evaporated. The residue is dissolved in toluene and extracted with a 10% hydrochloric acid. The aqueous acidic extract is made alkaline with a 40% sodium hydroxide solution to pH 12-13 and extracted with toluene. The toluene solution is dried and acidified with 31% ethanolic hydrogen chloride to pH 3. The precipitated crystalline product is filtered, washed with cold acetone and dried. Thus 2.05 g. of a product are obtained which is identical with the compound prepared according to Example 5. Yield: 40.6%.

EXAMPLE 7

To 10 g. (0.028 mole) of (−)-N-methyl-[2-(4-fluoro-phenyl)-1-methyl]-ethyl amine (+)-tartrate-dihydrate according to Example 5 a solution of 7.5 g. of sodium hydroxide in 25 ml. of water and 17 ml. of toluene are added. The mixture is stirred for 30 minutes. The phases are separated and the aqueous layer is extracted three times with 6 ml. of toluene each.

The toluene solution thus obtained is added to a solution of 1.37 g. of sodium hydroxide, 0.04 g. of benzyl triethyl ammonium chloride and 5 ml. of water. To the mixture 4.1 g. of propargyl bromide are added dropwise and the reaction mixture is stirred at room temperature for 15 hours. The phases are separated, the toluene layer is extracted twice with 7 ml. of 5% acetic acid each and twice with 10 ml. of 10% hydrochloric acid each. The aqueous-acidic extract is made alkaline by adding a 40% sodium hydroxide solution and is thereafter extracted with toluene. After drying the toluene solution is acidified to pH 3 with 31% ethanolic hydrogen chloride. The crystalline product is filtered, washed with cold acetone and dried. Thus 2.72 g. of a product are obtained which is identical with the compound prepared according to Example 5.

EXAMPLE 8

From 10 g. (0.028 mole) of (−)-N-methyl-[2-(4-fluoro-phenyl)-1-methyl]-ethyl amine (+)-tartrate dihydrate the base is set free as described in Example 7. To the dried toluene solution 24.7 g. (0.17 mole) of potassium carbonate are added whereupon a 60% toluene solution of 3.66 g. (0.03 mole) of propargyl bromide is added dropwise. The reaction mixture is stirred at room temperature and filtered. The toluene filtrate is extracted twice with 7 ml. of 5% acetic acid each and twice with 10 ml. of 10% hydrochloric acid each. The aqueous acidic extract is worked up according to Example 7. Thus 2.6 g. of a product are obtained which is identical with the compound prepared according to Example 5.

EXAMPLE 9

To a solution of 8.3 g. (0.05 mole) of (±)-N-methyl-[2-(4-fluoro-phenyl)-1-methyl]-ethyl amine, 5.4 g. (0.1 mole) of propargyl aldehyde and 100 ml. of 96% ethanol 3 g. of aluminium foils activated with mercury chloride are added in portions at 20°-30° C. The reaction mixture is stirred at room temperature for 24 hours, filtered and the filtrate is evaporated. The residue is dissolved in a 10% hydrochloric acid, extracted with benzene, made alkaline with a 40% sodium hydroxide solution and extracted again with benzene. The benzene solution is dried and evaporated. The residue is distilled off in vacuo at 2 Hgmm. Thus 5.6 g. of (±)-N-methyl-N-propynyl-[2-(4-fluoro-phenyl)-1-methyl]-ethyl amine are obtained. Bp.: 120°-123° C./2 Hgmm., $n_D^{20} = 1.5055$. The melting point of the hydrochloric amounts to 130°-132° C.

EXAMPLE 10

10 g. (0.065 mole) of 4-fluoro-phenyl acetone and 5.3 g. (0.097 mole) of propargyl amine are dissolved in 55 ml. of 96% alcohol. The solution is stirred for half an hour at 60° C. whereupon 1.75 g. of aluminium foil activated with mercury chloride are added. The reaction mixture is allowed to stand overnight, whereupon 15 ml. of a 40% sodium hydroxide solution are added, the alcohol is distilled off and the residue is extracted with benzene. The benzene solution is extracted with 10% hydrochloric acid, the aqueous acidic phase is made alkaline and extracted with benzene. After drying the benzene phase is evaporated and the residue is distilled off in vacuo. Thus 4.9 g. of (±)-N-propynyl-[2-(4-fluoro-phenyl)-1-methyl]-ethyl amine are obtained, yield 36%. Bp.: 134°-140° C./17 Hgmm., $n_D^{20} = 1.5031$.

4. g. of the above compound are dissolved in 25 ml. of acetone whereupon 4 g. of potassium carbonate and 4 g. of methyl iodide are added. The reaction mixture is refluxed for 2 hours, filtered and evaporated. The residue is dissolved in 10% hydrochloric acid, clarified, filtered, made alkaline with a 40% sodium hydroxide solution and extracted with toluene. After drying the toluene solution is acidified with ethanolic hydrogen chloride, the precipitated product is filtered and dried. Thus 3.1 g. of (±)-N-methyl-N-propynyl-[2-(4-fluoro-phenyl)-1-methyl]-ethyl amine hydrochloride are obtained, yield 131°-133° C.

EXAMPLE 11

To a solution of 6.0 g. (0.036 mole) of (±)-N-methyl-[2-(4-fluoro-phenyl)-1-methyl]-ethyl amine and 60 ml. of acetone 33.6 g. (0.24 mole) of potassium carbonate are added whereupon 7.45 g. (0.037 mole) of 2,3-dibromo-propene are added drop-wise at 25°–30° C. under stirring within 20–25 minutes. The reaction mixture is refluxed for 6 hours, filtered and evaporated. The residue is distilled off in vacuo at 4–5 Hgmm. Thus 6.52 g. of (±)-N-methyl-N-(2-bromo-propenyl-3)-[2-(4-fluoro-phenyl)-1-methyl]-ethyl amine are obtained, yield 63.3%. Bp.: 142°–143° C., $n_D^{20} = 1.5234$.

2.5 g. of the above product are dissolved in 35 ml. of ethanol whereupon 5 ml. of a 50% potassium hydroxide solution are added. The reaction mixture is refluxed for 16 hours and evaporated. The residue is taken up in water and extracted with benzene. After drying the benzene solution is acidified with ethanolic hydrogen chloride. The precipitated product is filtered and dried. Thus 2.2 g. of (±)-N-methyl-N-propynyl-[2-(4-fluor-phenyl)-1-methyl]-ethyl amine hydrochloride are obtained, mp.: 131°–133° C.

EXAMPLE 12

1.53 g. of N-2-[(p-fluoro-phenyl)-1-methyl]-ethyl-N-methyl amine are dissolved in 185 ml of anhydrous ethanol whereupon a solution of 3.66 g. of dibenzoyl-d-tartaric acid and 36 ml. of anhydrous ethanol is added. The precipitated white solid is filtered after two hours of standing and washed with anhydrous ethanol. Thus 1.6 g. of the salt are obtained, mp.: 180° C.

0.5 g. of the salt are suspended in 3.2 ml. of water, whereupon 1.3 ml. of 10% sodium hydroxide are added and the solution is extracted with ether. The ether extract is dried over anhydrous sodium sulfate and evaporated. Thus 0.3 g. of oily (±)-N-[p-fluoro-phenyl-1-methyl]-ethyl-N-methyl-amine base are obtained. $[\alpha]_D^{20} = +3.44°$ (ethanol).

The above product is propargylated according to the process described in Example 4. Thus optically active N-[2-(4-fluoro-phenyl)-1-methyl]-ethyl-N-methyl-N-propynyl-amine is obtained. The specific rotation of the hydrochloride is as follows:

$[\alpha]_D^{20} = +6.2°$ (ethanol, water),
$[\alpha]_D^{20} = 10.98°$ (water, c=2.9).

EXAMPLE 13

0.5 ml. of the solution of the test compound formed with anhydrous ethanol and having a suitable concentration is poured into a Petri-dish in which filter-paper discs (Whatman No. 1, diameter of 9 cm.) are placed. After evaporation of the solvent 15–20 flies (Musca domestica) under weak $CO_2$ narcosis are put into the Petri-dishes. The percental mortality is determined after 24 hours. Three replicates are used for each dose. The average values are summarized in Table 1.

TABLE 1

| Test compound | Dose (mg/disc) | | | |
|---|---|---|---|---|
| (hydrochloride) | 5.00 | 1.00 | 0.20 | 0.24 |
| N-benzyl-N-methyl-2-propynyl amine | 25 | 0 | 0 | 0 |
| N-methyl-N-propynyl-(2-phenyl-l-methyl)-ethyl amine | 55 | 24 | 8 | 0 |
| N-methyl-N-propynyl-(2-(3-methyl-phenyl)-1-methyl(-ethyl amine | 30 | 4 | 0 | 0 |
| N-methyl-N-propynyl-2-(4-bromo-phenyl)-1-methyl)-ethyl amine | 78 | 29 | 10 | 0 |
| N-propyl-N-(2-propynyl)-2-phenyl-1-methyl-ethyl amine | 0 | 0 | 0 | 0 |
| N-(2-propynyl)-2-phenyl-1-methyl-ethyl amine | 0 | 0 | 0 | 0 |

TABLE 1-continued

| Test compound | Dose (mg/disc) | | | |
|---|---|---|---|---|
| (hydrochloride) | 5.00 | 1.00 | 0.20 | 0.24 |
| N-(2-propynyl)-ethyl amine | 0 | 0 | 0 | 0 |
| N-methyl-N-(2-propynyl(-3-phenyl)-1-methyl-propyl amine | 0 | 0 | 0 | 0 |
| N-methyl-N-(2-propynyl)-3-(4-bromo-phenyl)-1-methyl-propyl amine | 0 | 0 | 0 | 0 |
| (+)N-methyl-N-propynyl-(2-4-fluoro-phenyl(-1-methyl)-ethyl amine | 100 | 35 | 20 | 2 |
| (+)-N-methyl-N-propynyl-(2-(4-fluoro-phenyl)-1-methyl)-ethyl amine | 100 | 45 | 24 | 2 |
| (−)-N-methyl-N-propynyl-(2-(4-fluoro-phenyl)-1-methyl)-ethyl amine | 100 | 30 | 20 | 2 |

EXAMPLE 14

The test compound is dissolved in cellosolve (Loba Chemie) and 0.3 μl microdrops of the said solution are applied onto $L_3$ house fly Musca domestica larvae. The killed insects are counted after 24 hours. The killed larvae are distinguished from the live individuals by pinning with an insect needle. The larvae which do not response to the piercing needle are considered to be mortal. Irrespective of the treatment about 5–10% of the larvae turned into pupae. In this case nymphs of normal shape and color are considered to be live while the elongated ones to be killed. Two replicates are carried out and 15 insects are used for each replicate. The results are summarized in the following Table II.

TABLE II

| Test compound | Dose μg/$L_3$ | | | | | |
|---|---|---|---|---|---|---|
| (hydrochloride) | 30 | 15 | 7.5 | 3.75 | 1.875 | 0.938 |
| | | | Mortality % | | | |
| N-benzyl-N-methyl--2-propynyl amine | 53 | 47 | 13 | 7 | 0 | 0 |
| (+)-N-methyl-N-propynyl-(2-4-bromo-pheyl-1-methyl)--ethyl amine | 100 | 80 | 20 | 7 | 3 | 0 |
| (+)-N-methyl-N-propynyl-(2-4-fluoro-phenyl-1-methyl)--ethyl amine | 100 | 100 | 85 | 48 | 25 | 0 |
| (+)-N-methyl-N-propynyl-(2-4-fluoro-phenyl-1-methyl)--ethyl amine | 100 | 100 | 90 | 50 | 27 | 0 |

EXAMPLE 15

*Drosophila melanogaster* larvae are cultured on a corn flour-yeast-agar nutrient medium comprising 200 ppm of the test compound. 200–250 eggs are placed on the nutrient medium and their growth is continuously observed. Three replicates are carried out at 26° C. Inhibition % is determined on the basis of the number of the $L_3$ larvae and the hatched-out imagos. The results are disclosed in Table III.

TABLE III

| Test compound | Inhibition % | |
|---|---|---|
| (hydrochloride) | $L_3$ | Imago |
| N-benzyl-N-methyl-2-propynyl amine | 58 | 75 |
| N-methyl-N-propynyl-(2-3--methyl-phenyl)-1-methyl)--ethyl amine | 75 | 88 |

TABLE III-continued

| Test compound | Inhibition % | |
|---|---|---|
| (hydrochloride) | L₃ | Imago |
| N-methyl-N-(2-propynyl)-3-phenyl-1-methyl-propyl amine | 42 | 60 |
| N-(2-propynyl)-2-phenyl-1-methyl-ethyl amine | 0 | 0 |
| N-methyl-N-propynyl-(2-(2-bromo-phenyl)-1-methyl)-ethyl amine | 80 | 88 |
| (+)-N-methyl-N-propynyl-(2-(4--fluoro-phenyl)-1-methyl)-ethyl amine | 100 | 100 |

EXAMPLE 16

Eggs of cabbage butterfly (*Pieris brassicae*) are placed on cabbage-leaves and the infected leaves are sprayed with solutions prepared according to formulation examples 13 and 15 (active ingredient content 0.02%).

After spraying the leaves are placed into Petri-dishes and after five days the inhibition % of hatching related to the control group is determined. The results obtained are set forth in Table IV.

TABLE IV

| Test compound | Inhibition % of hatching |
|---|---|
| N-benzyl-N-methyl-2-propynyl amine hydrochloride | 55 |
| N-(4-chloro-benzyl)-N-methyl--2-propynyl amine | 70 |
| N-methyl-N-propynyl-(2-(4-bromo-phenyl)-1-methyl)-ethyl amine hydrochloride | 85 |
| N-methyl-N-propynyl-(2-(4--fluoro-phenyl)-1-methyl)--ethyl amine hydrochloride | 100 |
| N-methyl-N-propynyl-(2-(4--fluoro-phenyl)-1-methyl)--ethyl amine | 100 |

In the following Examples the preparation of the insecticidal compositions of the present invention is shown.

EXAMPLE 17

A composition is prepared by methods known per se.

| Component | Amount, % by weight |
|---|---|
| Activeingredient (hydrochloride) | 20 |
| Sodium dioctyl sulfosuccinate | 5 |
| Vaseline oil (technical grade, 18%) | 18 |
| Octyl phenol polyglycol ether (EO = 3-5%) | 2 |
| Water ad | 100 |

EXAMPLE 18

80 SP water-soluble powder mixture

| Component | Amount, % by weight |
|---|---|
| Active ingredient (hydrochloride) | 80 |
| Sodium alkyl naphthalene sulfonate | 3 |
| Sodium lauryl sulfate | 2 |
| Nonyl phenol polyethylene glycol ether (EO = 23-30) | 1 |

EXAMPLE 19

25 EC emulsifiable concentrate

| Component | Amount, % by weight |
|---|---|
| Active ingredient (base) | 25 |
| Mixture of calcium alkyl aryl sulfonate and ethoxylated sorbitol hexaoleate | 10 |
| Mixture of aromatic solvents ad | 100 |

EXAMPLE 20

50 WP wettable powder

| Component | Amount, % by weight |
|---|---|
| Active ingredient (base) | 50 |
| Sodium ligno sulfonate | 6 |
| Mixture of ethoxylated polyethylene and polypropylene glycol | 2 |
| Sodium fatty alcohol sulfate | 1 |
| Calcium carbonate ad | 100 |

The compositions according to Examples 18–20 are prepared by methods of pesticidal industry known per se.

EXAMPLE 21

16.7 g of (±)-N-methyl-[2-(4-fluoro-phenyl)-1-methyl]-ethyl-amine are dissolved in 150 ml of acetone and 69.2 g of sodium-carbonate are added while stirring. On addition of 13.3 g of allyl-bromide the reaction mixture is refluxed for 8 hours, cooled and filtrated. The filtrate is evaporated and distilled in vacuo. 15.2 g of (±)-N-methyl-N-(2-propinyl)-[2-(4-fluoro-phenyl)-1 methyl]-ethylamine are obtained. The product is dissolved in 100 ml of carbone tetrachloride and 11.8 g of bromine are added dropwise. After stirring for 8 hours the solution is evaporated and the residue is dissolved in 400 ml of ethanol. 100 ml of a 50 w % aqueous sodium hydroxide solution are added and the reaction mixture is refluxed for 20 hours. On evaporation of the ethanol, water is added and the mixture is extracted with benzene. The benzene solution is extracted with 2N hydrochloric acid and on addition of a sodium hydroxide solution the extraction with benzene is repeated. The benzene extract is dried over sodium-sulphate, filtered and evaporated. On distillation in vacuo of the residue 5.6 g of (±)-N-methyl-N-(2-propynyl)-[2-(4-fluoro-phenyl)-1 methyl]-ethyl-amine are obtained.

Bp (0.6 Hgmm) 90°–93° C.

EXAMPLE 22

10 g of 4-fluoro-phenylacetone and 6.9 g of N-methyl-propargylamine are dissolved in 60 ml of 96% ethanol. 1.8 g aluminium sheet, (activated with mercury chloride) are added at 60° C. and the mixture is stirred for 10 hours, filtered and evaporated. The residue is dissolved in 10% hydrochloride acid and extracted with benzene. The aqueous layer is made alcaline and extracted with benzene, whereupon the benzene extract is dried and evaporated. The residue is distilled in vacuo. 5.1 g of (±)-N-methyl-N-(2-propinyl)-(2-(4-fluorophenyl)-1 methyl)-ethylamine are obtained.

Bp: (2 Hgmm)=120°–123° C., $n_D^{20}$=1,5058.

EXAMPLE 23

1.72 g of 1-(4-fluoro-phenyl)-2-chloro-propane (Acta Chim. Acad. Sci. Hung 79 (1973) 433) and 1.4 g of N-methyl-propargyl-amine are heated in a sealed tube for 5 hours. The reaction mixture is dissolved in 30% aqueous ethanol containing hydrochloric acid and evaporated. From the residue 0.35 g of (±)-N-methyl-N-(2-propinyl)-[2-(4-fluoro-phenyl)-1-methyl]-ethyl-amine hydrochloride are obtained.

Mp: 130°–132° C.

What we claim is:

1. A method of combatting insects which comprises applying onto plants to be protected or onto the insects or the environment thereof an effective amount of a pesticidal composition which comprises a compound selected from the group consisting of N-{2-(4-fluoro-phenyl)-1-methyl}-ethyl-N-methyl-N-propynyl amine, its optical isomers, and its acid addition salts, as an active ingredient.

2. The method for combatting insects defined in claim 1 wherein the insect to be treated is musca domestica or musca domestica larvae.

3. The method for combatting insects defined in claim 2 wherein the musca domestica or musca domestica larvae is treated by a dose of 7.5 to 30 micrograms of said compound/insect.

* * * * *